United States Patent
Conley et al.

(10) Patent No.: US 9,205,161 B2
(45) Date of Patent: Dec. 8, 2015

(54) DISINFECTING COMPOSITION COMPRISING A CHLORAMINE BLEACHING AGENT FOR REMOVABLE DENTAL APPLIANCES

(71) Applicants: Nicholas Conley, Cupertino, CA (US); Lynn Muzik, Cupertino, CA (US)

(72) Inventors: Nicholas Conley, Cupertino, CA (US); Lynn Muzik, Cupertino, CA (US)

(73) Assignee: LMA Solutions, Inc., Cupertino, CA (US)

( * ) Notice: Subject to any disclaimer, the term of this patent is extended or adjusted under 35 U.S.C. 154(b) by 0 days.

(21) Appl. No.: 14/600,869

(22) Filed: Jan. 20, 2015

(65) Prior Publication Data
US 2015/0258231 A1    Sep. 17, 2015

Related U.S. Application Data

(63) Continuation-in-part of application No. 14/213,672, filed on Mar. 14, 2014, now Pat. No. 8,937,036.

(51) Int. Cl.
| A61Q 11/00 | (2006.01) |
| A61Q 11/02 | (2006.01) |
| C11D 3/395 | (2006.01) |
| C11D 7/34  | (2006.01) |
| A61L 2/18  | (2006.01) |
| A01N 43/84 | (2006.01) |
| A01N 47/40 | (2006.01) |

(52) U.S. Cl.
CPC . *A61L 2/18* (2013.01); *A01N 43/84* (2013.01); *A01N 47/40* (2013.01)

(58) Field of Classification Search
CPC ........ C11D 3/395; C11D 3/3953; C11D 7/34; C11D 17/0047; A61K 6/0035; A61Q 11/00; A61Q 11/02
See application file for complete search history.

(56) References Cited

U.S. PATENT DOCUMENTS

| 4,362,639 A | 12/1982 | Eoga |
| 4,552,679 A | 11/1985 | Schobel et al. |
| 4,568,560 A * | 2/1986 | Schobel ................. A61K 8/922 424/401 |
| 5,486,304 A | 1/1996 | Eoga et al. |
| 6,153,567 A | 11/2000 | Hughes |
| 7,199,082 B1 * | 4/2007 | Chapman ................. A01N 3/00 504/115 |
| 8,044,008 B2 | 10/2011 | Muzik et al. |
| 2005/0032668 A1 | 2/2005 | Pedersen et al. |
| 2007/0054830 A1 | 3/2007 | Dullea et al. |
| 2008/0075686 A1 | 3/2008 | Fujii et al. |
| 2009/0042756 A1 * | 2/2009 | Muzik .................... A01N 59/00 510/100 |
| 2011/0100371 A1 | 5/2011 | Michael et al. |
| 2012/0125847 A1 * | 5/2012 | Sehgal .................... A61L 2/022 210/639 |
| 2013/0323308 A1 * | 12/2013 | Simpkins ................ A61K 9/107 424/490 |
| 2014/0065627 A1 * | 3/2014 | Whitney .................. A01N 1/00 435/6.12 |

OTHER PUBLICATIONS

International Search Report and Written Opinion as mailed on Jun. 29, 2015 for International Application No. PCT/US2015/020824.

* cited by examiner

*Primary Examiner* — Charles Boyer
(74) *Attorney, Agent, or Firm* — Dale F. Regelman; Quarles & Brady LLP

(57) ABSTRACT

A composition for disinfecting removable dental appliances, which includes a chloramine bleaching agent, and an amino-substituted alkylsulfonic acid.

20 Claims, 2 Drawing Sheets

DISINFECTING COMPOSITION COMPRISING A CHLORAMINE BLEACHING AGENT FOR REMOVABLE DENTAL APPLIANCES

CROSS REFERENCE TO RELATED APPLICATIONS

This Application is a Continuation-In-Part Application of U.S. Non-Provisional Application having Ser. No. 14/213,672 filed Mar. 14, 2014, now U.S. Pat. No. 8,937,036, U.S. Non-Provisional application Ser. No. 14/213,672, now U.S. Pat. No. 8,937,036, is hereby incorporated by reference.

FIELD OF THE INVENTION

The invention described herein relates to a composition for disinfecting dental appliances, such as retainers, night guards, removable braces, and dentures, and method using same.

BACKGROUND OF THE INVENTION

The accumulation of residues on dental appliances (e.g., removable braces, retainers, night guards, removable braces, dentures, etc.) is a familiar and persistent problem for wearers of such appliances. These residues often consist of some combination of food particles and biofilm (i.e., plaque), the latter of which is a slime layer that naturally develops when bacteria attach to an inert support. Many of these bacteria produce volatile sulfur compounds as waste products. If the dental appliance is not rid of food particles and biofilm on a regular basis, the malodorous waste products will accumulate, causing the wearer to exhibit bad breath. Even more serious is the potential for pathogenic bacteria to inhabit the biofilm, increasing the likelihood of infection for the wearer.

The majority of commercially available effervescent dental appliance cleansing tablets are based on alkaline peroxysalts (e.g., those sold under the tradename EFFERDENT), which provide excellent bleaching action but poor plaque removal, as described in U.S. Pat. No. 4,552,679. An additional shortcoming of alkaline peroxysalts is their documented health risk. After seventy-three severe reactions and at least one death, the U.S. Food and Drug Administration issued a statement on Feb. 14, 2008 asking the manufacturers of denture cleansers to revise labeling and to consider appropriate alternatives to persulfate, a common alkaline peroxysalt found in many brands, including EFFERDENT. All peroxysalts share a common mode of operation (i.e., liberation of hydrogen peroxide upon contact with water) and a similar structural feature (i.e., an associated molecule of hydrogen peroxide). Therefore, it is an object of the present invention to provide a dental appliance cleansing composition that does not include peroxysalts. Examples of powders and tablets incorporating alkaline peroxysalts can be found in U.S. Pat. Nos. 4,362,639, 4,552,679, and 5,486,304, and U.S. Patent Application 20070054830.

U.S. Pat. No. 8,044,008 to Muzik et at ("the Muzik composition") represents the most efficacious prior art composition. A shortcoming of the Muzik composition, however, is a high concentration of a chloramine bleaching agent, namely from 1 percent to 20 percent by weight of the composition. Upon dissolution of the composition in water, a pH-dependent equilibrium is established between the chloramine bleaching agent, hypochlorous acid, and hypochlorite ion. However, upon dissolution of the composition in water, hypochlorous acid also imparts a chlorine-like odor that is reminiscent of swimming pools. Muzik et al. teach the use of a fragrance at up to about 3 percent by weight of the composition "to mask any chlorine odor originating from the dental appliance cleansing formula." Unfortunately, high liquid fragrance loadings (greater than about 1.5 percent) can introduce aggregation of solids in the formula ("caking") and slow dissolution. In addition, fragrance represents one of the most expensive raw materials costs in the manufacture of the composition. Therefore, a need persists for a composition that is effective at disinfecting and removing biofilm from dental appliances without suffering from the shortcomings of chlorine-like odor and/or the requirement for high fragrance loadings.

SUMMARY OF THE INVENTION

A composition for disinfecting removable dental appliances is disclosed, wherein that composition includes a chloramine bleaching agent, and an amino-substituted alkylsulfonic acid. A additive package for a cleaning formulation to enhance the anti-microbial efficacy thereof is disclosed, wherein the additive package consists essentially of a chloramine bleaching agent and an amino-substituted alkylsulfonic acid. A method for disinfecting removable dental appliances is disclosed, wherein that method includes forming an aqueous solution of a disinfecting composition comprising a chloramine bleaching agent and an amino-substituted alkylsulfonic acid, and placing the removable dental appliance in the aqueous solution, and after about 5 minutes removing the removable dental appliance from the aqueous solution.

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION OF PREFERRED EMBODIMENTS

Figures 1A, 1B, 1C:
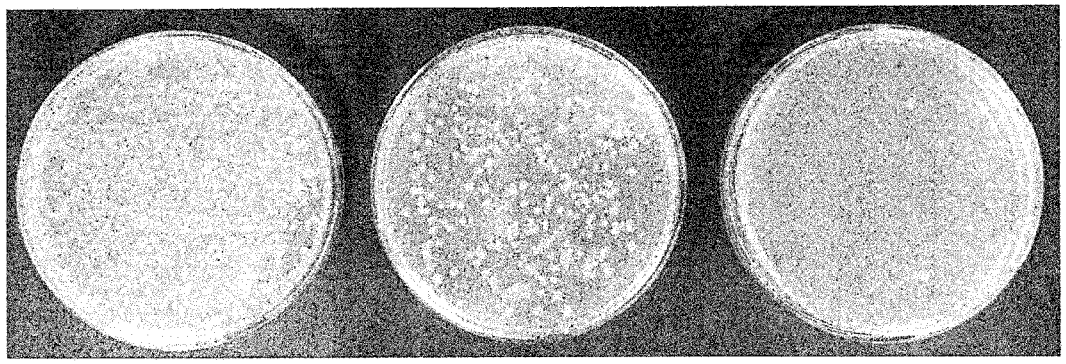
FIG. 1A is a photograph of an LB Agar plate treated with 2-(N-Morpholino)ethanesulfonic Acid-only at a plating dilution of $1:1\times10^4$ and incubated for 20 hours at 37° C.
FIG. 1B is a photograph of an LB Agar plate treated with Sodium Dichloroisocyanurate-only at a plating dilution of 1:10 and incubated for 20 hours at 37° C.
FIG. 1C is a photograph of an LB Agar plate treated with MES and NaDCC at a plating dilution of 1:10 and incubated for 20 hours at 37° C.

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Applicants' composition represents a significant improvement over the prior art, particularly Muzik et al. To remedy deficiencies in the prior art, Applicants' improved composition comprises (a) a chloramine bleaching agent, (b) a surfactant, (c) a water-soluble carboxylic acid, (d) an alkaline base (e) a chelating agent for alkaline earth metal ions, and (f) an amino acid.

Optional components may be added to the composition to facilitate its storage and handling, and to make it more pleasing to the user. These optional components include, but are not limited to, a fragrant substance, an indicator dye, an anti-caking agent, a tablet binder, and a lubricant.

In certain embodiments, Applicants' "amino" acid comprises an amino-substituted alkyl sulfonic acid I.

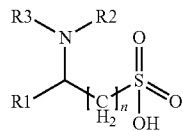

In certain embodiments, R1 is selected from the group consisting of —H, —CH$_3$, and phenyl. In certain embodiments, R2 is selected from the group consisting of —H, alkyl, and phenyl. In certain embodiments, R3 is selected from the group consisting of —H, alkyl, and phenyl. In certain embodiments, n is 0 to about 4.

In certain embodiments, the amino moiety of Applicants' amino-substituted alkyl sulfonic acid component comprises a secondary amine. In certain embodiments, the amino moiety of Applicants' amino-substituted alkyl sulfonic acid comprises a tertiary amine.

In certain embodiments, the —N(R2)(R3) moiety of Applicants' amino-substituted alkyl sulfonic acid comprises a cyclic structure. In certain embodiments, the —N(R2)(R3) moiety of Applicants' amino-substituted alkyl sulfonic acid comprises a morpholino group. In certain embodiments, the —N(R2)(R3) moiety of Applicants' amino-substituted alkyl sulfonic acid comprises a pyrrolidino group. In certain embodiments, the —N(R2)(R3) moiety of Applicants' amino-substituted alkyl sulfonic acid comprises a piperidino group. In certain embodiments, the —N(R2)(R3) moiety of Applicants' amino-substituted alkyl sulfonic acid comprises a piperazino group.

In certain embodiments, amino-sulfonic acid I comprises 3-(N-morpholino)propanesulfonic acid ("MOPS"), wherein R1 is —H, R2 and R3 in combination comprise —N morpholino, and n is 2. In certain embodiments, amino-sulfonic acid I comprises 2-(N-morpholino)ethanesulfonic acid ("MES"), wherein R1 is —H, R2 and R3 in combination comprise —N morpholino, and n is 1.

In certain embodiments, Applicants' composition comprises from about 0.001 percent to about 20 percent by weight of the MOPS and/or MES additive. In certain embodiments, Applicants' composition comprises from about 0.02 percent to about 10 percent by weight of the MOPS and/or MES additive. In certain embodiments, Applicants' composition comprises from about 0.015 percent to about 0.025 percent by weight of the MOPS and/or MES additive.

The "chloramine bleaching agent" is any chemical compound containing one or more chlorine-nitrogen bonds that liberates hypochlorous acid upon contact with water. Examples of chloramine bleaching agents include, but are not limited to, sodium dichloroisocyanurate and sodium trichloroisocyanurate, and include both the salt and acid forms. Other chloramine bleaching agents are well known in the art and are equally suitable. In certain embodiments, Applicants' composition comprises from about 0.01 percent to about 20 percent by weight of the chloramine bleaching agent. In certain embodiments, Applicants' composition comprises from about 0.2 percent to about 10 percent by weight of the chloramine bleaching agent. In certain embodiments, Applicants' composition comprises from about 0.4 percent to about 0.6 percent by weight of the chloramine bleaching agent.

The "surfactant" is any organic compound that contains at least one hydrophobic functional group and one hydrophilic functional group (i.e., an amphiphilic compound). The surfactants may be ionic or non-ionic in nature. Examples of surfactants include, but are not limited to, sodium dodecyl sulfate, sodium laureth sulfate, sodium dodecylbenzenesulfonate, alkyl polyl(ethylene oxide), and cetyl alcohol. Other surfactants are well known in the art and are equally suitable. In certain embodiments, Applicants' composition comprises from about 0.1 percent to about 10 percent by weight of the surfactant. In certain embodiments, Applicants' composition comprises from about 2 percent to about 5 percent by weight of the surfactant. In certain embodiments, Applicants' composition comprises from about 3.5 percent to about 4.5 percent by weight of the surfactant.

The "water-soluble carboxylic acid" is any compound containing one or more carboxylic acid functional groups (i.e., —COOH) and a solubility in water greater than about 20 g/L. Examples of suitable carboxylic acids include, but are not limited to, oxalic acid, malonic acid, malic acid, maleic acid, and citric acid. Other water-soluble carboxylic acids are well known in the art and are equally suitable. In certain embodiments, Applicants' composition comprises from about 70 percent by weight of the water-soluble carboxylic acid. In certain embodiments, Applicants' composition comprises from about 30 percent to about 50 percent by weight of the water-soluble carboxylic acid. In certain embodiments, Applicants' composition comprises from about 40 percent to about 44 percent by weight of the water-soluble carboxylic acid.

The "alkaline base" is the basic salt of any alkali metal or alkaline earth metal. Examples of suitable alkaline bases include, but are not limited to, sodium carbonate, sodium bicarbonate, sodium hydroxide, potassium carbonate, potassium bicarbonate, potassium hydroxide, calcium carbonate, and magnesium hydroxide. Other alkaline bases are well known in the art and are equally suitable. It should be noted that the alkaline base need not be soluble in water.

In certain embodiments, Applicants' composition comprises from about 5 percent to about 40 percent by weight of the alkaline base. In certain embodiments, Applicants' composition comprises from about 22 percent to about 32 percent by weight of the alkaline base. In certain embodiments, Applicants' composition comprises from about 26 percent to about 28 percent by weight of the alkaline base.

The "chelating agent" is any compound that binds to alkaline earth metal ions, especially calcium and magnesium, and forms a complex that exhibits some degree of water solubility. Examples of suitable chelating agents include, but are not limited to, tetrasodium pyrophosphate, sodium tripolyphosphate, sodium tetraphosphate, sodium hexametaphosphate, ethylenediaminetetraacetic acid, and ethylene glycol tetraacetic acid. Other chelating agents are well known in the art and are equally suitable. In certain embodiments, Applicants' composition comprises from about 1 percent to about 30 percent by weight of the chelating agent. In certain embodiments, Applicants' composition comprises from about 10 percent to about 20 percent by weight of the chelating agent. In certain embodiments, Applicants' composition comprises from of about 14 percent to about 16 percent by weight of the chelating agent.

Applicants have found that the amino acid component dramatically potentiates the disinfecting properties of the chloramine bleaching agent, allowing the latter to be incorporated at lower percentages, which reduces the chlorine-like odor of the composition upon dissolution in water.

It is also believed that the amino moiety of the amino-acid forms an N—Cl bond with chlorine from hypochlorous acid (formed upon dissolution of the composition in water) and reduces the concentration of the hypochlorous acid species, which is responsible for the chlorine-like odor.

The following examples are presented to further illustrate to persons skilled in the art how to make and use the invention. These examples are not intended as a limitation, however, upon the scope of the invention.

Example I

The composition recited in Table 1 was used in this Example I.

TABLE 1

| COMPONENT | GRAMS Per Dose |
|---|---|
| Sodium Dichloroisocyanurate | 0.013 |
| Sodium Dodecyl Sulfate | 0.096 |
| Anhydrous Citric Acid | 1.057 |
| Anhydrous Sodium Carbonate | 0.673 |
| Sodium Tripolyphosphate | 0.384 |
| Anhydrous Sodium Sulfate | 0.248 |
| 2-(N-Morpholino)ethanesulfonic Acid | 0.00048 |

To the composition was added 100 ml of tap water, and vigorous effervescence occurred. A DOCTOR'S brand plastic night guard, which was coated with an accumulated layer of biofilm from normal wear, was added to this solution. After 5 minutes, the appliance was removed, rinsed briefly with water, and stained with an FD&C Red 20 plaque disclosing dye tablet. No staining was noted, indicating that the biofilm had been removed by soaking in a solution of the composition.

A nearly identical night guard was used as a positive control (it was soaked in plain tap water only) and showed extensive staining.

Example II

The purpose of this study was to evaluate the bactericidal effect of the Applicant's formulation of Example I against a representative panel of relevant oral bacteria at recommended consumer use conditions for dilution of product, temperature of solution, and contact time. Two and a half grams of the composition of EXAMPLE I were dissolved in 80 mL of water to form an aqueous solution.

EXPERIMENTAL 4.1 Stock Organism Preparation 4.1.1 Seed-lot culture maintenance techniques were used so that the viable microorganisms used for inoculation was not more than 3 passages removed from the original master seed-lot and no older than 15 days from its preparation date. Each strain was grown as recommended by ATCC or with past experience.

4.3.3 The cell concentration (CFU/ml) was determined in all working organism suspensions by serial dilution and plating. 10-fold serial dilutions were prepared by using 1.0 ml of suspension into 9.0 mL of PBS.

4.3.3.1 For *K. pneumoniae*: The dilutions of each culture were prepared up to $10^{-7}$. Duplicate pour plates were prepared by using 1.0 mL from the dilution test tubes of $10^{-5}$, $10^{-6}$, and $10^{-7}$ with Soybean Casein Digest Agar with lecithin and Polysorbate 80 agar. The plates were incubated at 32.5±2.5° C.

Time Kill Study 4.5.1 Product was tested in triplicate and plated in duplicate.

4.5.2 100 mL of sterile DI water was added to each of six 250 mL wide mouth sterile flasks or sterile containers. The flasks was covered and placed in a water bath set at 32.5±2° C. for 30 minutes to equilibrate.

4.5.3 Two flasks were removed from the water bath and wiped down with 70% isopropanol. Each flask was inoculated with 2.0 mL of the working organism suspension. One packet of Applicants" composition of Example 1 was added to one flask. This was time zero (T=0).

4.5.3.1 T=0 organism suspension control was plated. 1.0 mL as removed from the control flask and added to 9.0 mL of D/E Neutralization Broth ($10^{-1}$). 10-fold serial dilutions were mixed and prepared in D/E Neutralizing broth to $10^{-6}$. Duplicate pour plates were prepared for each dilution using 1.0 mL for each plate with agar.

4.5.4 At 5 minutes±10 seconds and at 30 minutes±10 seconds, 1.0 mL aliquot was removed from the product sample flask and added to 9.0 mL of D/E Neutralizing Broth. This is $10^{-1}$ dilution.

4.5.5 Additional 10-fold serial dilutions were performed to $10^{-4}$ in D/E Neutralizing Broth. The tubes were vortex mixed between each dilution.

4.5.6 From both the product sample and control tubes, 10-fold serial dilutions were prepared to $10^{-3}$ in D/E Neutralizing Broth. Duplicate pour plates were prepared directly from each of the dilution and control tubes by using 1.0 mL for all organisms.

4.5.7 All plates were incubated at 32.5±2.5° C.

4.5.8 At the end of incubation, the plates from the dilution that achieved the countable range of 25-250 CFU/plate were counted. The average count was determined by multiplying the dilution factor then calculated to the $\log_{10}$ value.

4.5.9 Steps 4.5.3 to 4.5.7 was repeated for the remaining (2) samples.

4.5.10 At the end of incubation, the plates from the dilution that achieved the countable range of 25-250 CFU/plate were counted. The average count was multiplied by the dilution factor then calculates the $\log_{10}$ value.

4.5.11 The log reduction was calculated by subtracting the $\log_{10}$ value of the organisms surviving the product sample after the desired contact time from the $\log_{10}$ value of the organism suspension control.

4.5.12 Applicants set a minimum acceptable residual bactericidal concentration as log 3 reduction from the initial inoculum. Applicants' formulation of Example 1 did achieve more than a log 3 reduction at the 5 minutes time intervals for all organisms tested.

Results

Table 2 recites data for the anti-microbial efficacy of Applicants' formulation of Example 1 for *K. pneumoniae* after 5 and 30 minute exposures. Applicants' formulation of Example 1 showed greater than an average log 4.4 reduction in *K. pneumoniae* CFU/mL after either 5 or 30 minute exposures.

TABLE 2

| Time | Inoculums (CFU/mL) | | % Reduction | | Log reduction | |
|---|---|---|---|---|---|---|
| | Control | Product | Control | Product | Control | Product |
| Initial | 2.3E5 | 2.3E5 | N/A | N/A | N/A | N/A |
| 5 min | 1.3E5 | <1.0E1 | 43.5% | >99.9% | 0.2 | >4.4 |
| 30 min | 1.5E5 | <1.0E1 | 34.8% | >99.9% | 0.2 | >4.4 |

Example III

A working suspension of BL21 *E. coli* cells in LB broth ($1.16 \times 10^8$ CFU/ml) was contacted for 15 min at 37° C. with either 1×PBS buffer (control), 2-(N-morpholino)ethanesulfonic acid ("MES") (final conc. of 25 µM or 0.0049 mg/ml), Sodium Dichloroisocyanurate ("NaDCC") (final conc. of 0.9 mg/ml), or MES (final conc. of 25 µM or 0.0049 mg/ml)+NaDCC (final conc. of 0.9 mg/ml). Lysogeny broth (LB), a nutritionally rich medium, is primarily used for the growth of bacteria.

After contact, ten-fold serial dilutions from 1:10 to $1:10^6$ were prepared using D/E neutralizing broth and an aliquot at each dilution (100 µl) was plated onto an LB agar plate and incubated for 20 hours at 37° C.

The plate shown in FIG. 1A corresponds to treatments with MES-only at a plating dilution of $1:1\times10^4$. The plate shown in FIG. 1B corresponds to treatments with NaDCC-only at a plating dilution of 1:10. The plate shown FIG. 1C corresponds to treatment with MES+NaDCC at plating dilution of 1:10.

The PBS control plate is not shown, but has a similar number of colony-forming units (CFU) as the MES-only plate (FIG. 1A). As can be observed from a comparison of FIGS. 1A, 1B, and 1C, a previously unreported synergistic effect on bacterial kill is achieved by combining MES and NaDCC.

Table 3 recites data showing the synergistic effect on bacterial kill achieved by combining MES and NaDCC as described in Example 3.

TABLE 3

| Sample | Exposure time (min) | Plate count (CFU)* | Plate dilution (1:x) | CFU/ml | | % Reduction | | Log reduction | |
|---|---|---|---|---|---|---|---|---|---|
| | | | | Control | Product | Control | Product | Control | Product |
| PBS control | 15 | 116 | 1.0E+05 | 1.16E+08 | 1.16E+08 | 0.00 | 0.0000 | 0.00 | 0.00 |
| MES only | 15 | 128 | 1.0E+05 | 1.16E+08 | 1.28E+08 | 0.00 | −10.3448 | 0.00 | −0.04 |
| NaDCC only | 15 | 331 | 1.0E+01 | 1.16E+08 | 3.31E+04 | 0.00 | 99.9715 | 0.00 | 3.54 |
| MES + NaDCC | 15 | 2 | 1.0E+01 | 1.16E+08 | 2.00E+02 | 0.00 | 99.9998 | 0.00 | 5.76 |

*100 ul volume plated

Figures 2A, 2B:
FIG. 2A is a photo showing Applicants formulation of Example I immediately upon contact with indigo carmine dye (FD&C Blue No. 2)
FIG. 2B is a photo showing Applicants' formulation of Example I 45 seconds after contact with the indigo carmine dye.

The use of 2-(N-morpholino)ethanesulfonic acid ("MES") in combination with Sodium Dichloroisocyanurate ("NaDCC") results in up to a 1000-fold acceleration in bleaching rate of common dyes with respect to NaDCC alone, including food and beverage stains, with only 0.02 weight percent MES loading. For example and referring now to FIGS. 2A and 2B. FIG. 2A is a photo showing Applicants" formulation of Example I immediately upon contact with indigo carmine dye (FD&C Blue No. 2). FIG. 2B is a photo showing Applicants' formulation of Example I 45 seconds after contact with the indigo carmine dye. Without the MES additive, a prior art composition required several hours after contact with the indigo carmine dye before the prior art formulation turned colorless.

The use of 2-(N-morpholino)ethanesulfonic acid ("MES") in combination with Sodium Dichloroisocyanurate ("NaDCC") enables at least a 50 weight percent reduction in NaDCC levels without sacrificing stain-removal performance on industry-standard stain panel tests. For example, in Example 1 of U.S. Pat. No. 8,044,008, sodium dichloroisocyanurate is used at about 4.0 weight percent. In this Example from the '008 Patent, the formulation of Example 1 did not contain any MES.

In Example I hereof, sodium dicloroisocyanurate is used at about 0.5 weight percent in combination with MES at 0.02 weight percent. Thus, the formulation of Example 1 herein uses sodium dichloroisocyanurate at about ⅛th of the weight percentage recited in the '008 Patent.

The use of 2-(N-morpholino)ethanesulfonic acid ("MES") in combination with Sodium Dichloroisocyanurate ("NaDCC") maintains bactericidal efficacy with at least a 50 weight percent reduction in bleaching agent as evidenced by a greater than log 4 reduction at 5 minute contact time with *Klebsiella pneumoniae*.

The reduced levels of the chloramine bleaching agent obviate the need for a fragrance to cover an offending "chlorine smell." In certain embodiments, Applicants' disinfecting composition includes no fragrance. In certain embodiments Applicants' additive package includes no fragrance.

In certain embodiments, Applicants' disinfecting composition includes no peroxysalts. In certain embodiments, Applicants' additive package includes no peroxysalts.

Example 4

In certain embodiments, an additive package consisting of MES and NaDCC can be added to a commercial cleaning formulation, such as and without limitation a commercial dental appliance cleaning formulation, to increase the anti-microbial efficacy of that commercial cleaning formulation. In certain embodiments Applicants' additive package consists essentially of MES and NaDCC, but includes minor amounts of one or more excipients, such as for example, a drying agent.

Applicants' additive package can be added to a commercial cleaning formulation such that the MES and the NaDCC comprise about the same weight percentage loadings in that composite formulation as MES and NaDCC comprise in Example III hereof.

While the preferred embodiments of the present invention have been illustrated in detail, it should be apparent that modifications and adaptations to those embodiments may occur to one skilled in the art without departing from the scope of the present invention as set forth herein.

We claim:

1. A composition for disinfecting removable dental appliances, consisting essentially of:
    a chloramine bleaching agent;
    an amino-substituted alkylsulfonic acid;
    a surfactant;
    a chelating agent for alkaline earth metal ions; and
    a drying agent,
    wherein exposure of said removable dental appliance for 5 minutes in an aqueous solution of said composition results in greater than a log 4 reduction in bacterial levels.

2. The additive package of claim 1, wherein said amino-substituted alkylsulfonic acid comprises the structure:

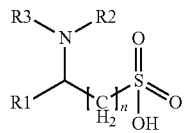

wherein R1 is selected from the group consisting of —H, —CH$_3$, and phenyl, R2 is selected from the group consisting of —H, alkyl, and phenyl, R3 is selected from the group consisting of —H, alkyl, and phenyl, and n is 0 to about 4.

3. The additive package of claim 2, wherein the amino moiety of said amino-substituted alkyl sulfonic acid comprises a secondary amine.

4. The additive package of claim 2, wherein the amino moiety of said amino-substituted alkyl sulfonic acid comprises a tertiary amine.

5. The additive package of claim 4, wherein the —N(R2)(R3) moiety of said amino-substituted alkyl sulfonic acid comprises a cyclic structure.

6. The additive package of claim 5, wherein the —N(R2)(R3) moiety of said amino-substituted alkyl sulfonic acid is selected from the group consisting of a morpholino group, a pyrrolidino group, a piperidino group, and a piperazino group.

7. The additive package of claim 2, wherein R1 is hydrogen and n is 1.

8. The additive package of claim 2, wherein R1 is hydrogen and n is 2.

9. The disinfecting composition of claim 1, further comprising:
    water soluble carboxylic acid; and
    an alkaline base.

10. The disinfecting composition of claim 1, wherein said disinfecting composition does not contain a peroxysalt.

11. A method for disinfecting removable dental appliances, comprising:
    forming an aqueous solution of a disinfecting composition according to present claim 1;
    placing said removable dental appliance in said aqueous solution; and
    after about 5 minutes, removing said removable dental appliance from said aqueous solution;
    wherein exposure of said removable dental appliance for 5 minutes in said aqueous solution results in greater than a log 4 reduction in bacterial levels.

12. The method of claim 11, wherein said amino acid comprises an amino-substituted alkylsulfonic acid having the structure:

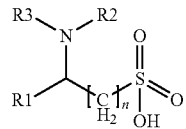

and wherein R1 is selected from the group consisting of —H, —CH$_3$, and phenyl, R2 is selected from the group consisting of —H, alkyl, and phenyl, R3 is selected from the group consisting of —H, alkyl, and phenyl, and n is 0 to about 4.

13. The method of claim 12, wherein the amino moiety of said amino-substituted alkyl sulfonic acid comprises a secondary amine.

14. The method of claim 13 wherein the amino moiety of said amino-substituted alkyl sulfonic acid comprises a tertiary amine.

15. The method of claim 12, wherein the —N(R2)(R3) moiety of said amino-substituted alkyl sulfonic acid comprises a cyclic structure.

16. The method of claim 15, wherein the —N(R2)(R3) moiety of said amino-substituted alkyl sulfonic acid is selected from the group consisting of a morpholino group, a pyrrolidino group, a piperidino group, and a piperazino group.

17. The method of claim 12, wherein R1 is hydrogen and n is 1.

18. The method of claim 12, wherein R1 is hydrogen and n is 2.

19. The method of claim 11, wherein said disinfectant composition further comprises:
    a water soluble carboxylic acid; and
    an alkaline base.

20. The method of claim 11, wherein said disinfecting composition does not contain a peroxysalt.

* * * * *